United States Patent
Nikoonahad et al.

(10) Patent No.: US 6,411,390 B1
(45) Date of Patent: Jun. 25, 2002

(54) INTERFEROMETRIC SYSTEM FOR MEASUREMENT DISTURBANCE OF A SAMPLE

(75) Inventors: Mehrdad Nikoonahad, Menlo Park; John Yifu Jiang, Cupertino, both of CA (US)

(73) Assignee: Kla-Tencor Corporation, San Jose, CA (US)

( * ) Notice: Subject to any disclaimer, the term of this patent is extended or adjusted under 35 U.S.C. 154(b) by 0 days.

(21) Appl. No.: 09/499,557

(22) Filed: Feb. 7, 2000

Related U.S. Application Data (63) Continuation of application No. 09/166,614, filed on Oct. 5, 1998, now abandoned.

(51) Int. Cl.$^7$ .............................................. G01B 9/02
(52) U.S. Cl. .................... 356/502; 356/432 T; 356/486
(58) Field of Search .................... 356/349, 357, 356/432 T, 502, 503, 485, 486; 73/655, 657, 800

(56) References Cited

U.S. PATENT DOCUMENTS

| | | | |
|---|---|---|---|
| 3,796,495 A | * | 3/1974 | Laub ......................... 356/109 |
| 4,255,971 A | | 3/1981 | Rosencwaig |
| 4,521,118 A | | 6/1985 | Rosencwaig |
| 4,522,510 A | | 6/1985 | Rosencwaig et al. |
| 4,581,939 A | | 4/1986 | Takahashi |
| 4,619,529 A | * | 10/1986 | Iuchi et al. .................. 356/358 |
| 4,679,946 A | | 7/1987 | Rosencwaig et al. |
| 4,854,710 A | | 8/1989 | Opsal et al. |
| 4,952,063 A | | 8/1990 | Opsal et al. |
| 4,968,144 A | | 11/1990 | Thomas et al. |
| 5,042,952 A | | 8/1991 | Opsal et al. |
| 5,074,669 A | | 12/1991 | Opsal |
| 5,149,978 A | | 9/1992 | Opsal et al. |
| 5,206,710 A | | 4/1993 | Geiler et al. |
| 5,228,776 A | | 7/1993 | Smith et al. |
| 5,298,970 A | | 3/1994 | Takamatsu et al. |
| 5,479,259 A | * | 12/1995 | Nakata et al. ............... 356/349 |
| 5,608,526 A | | 3/1997 | Piwonka-Corle et al. |
| 5,706,094 A | | 1/1998 | Maris |
| 5,748,318 A | | 5/1998 | Maris et al. |
| 6,108,087 A | * | 8/2000 | Nikoonahad et al. ........ 356/359 |

OTHER PUBLICATIONS

Dual–Probe Laser Interferometer, Huang et al, Journal of the Acoustical Societ of America, Sep. 1991, pp 1269–1274.*
"Photothermal Radiometry of Semiconductors," S. Sheard et al., published in the text book *Progress in Photothermal and Photoacoustic Science and Technology*, vol. II, Non–Destructive Evaluation (NDE), A. Mandelis, Editor, Prentice Hall, 1994, pp. 112–150.

(List continued on next page.)

Primary Examiner—Frank G. Font
Assistant Examiner—Andrew H. Lee
(74) Attorney, Agent, or Firm—Skjerven Morrill MacPherson LLP (57) ABSTRACT

A pump beam is modulated at a first frequency and a modulated pump beam is used to periodically heat the surface of a semiconductor wafer at a location, thereby generating a disturbance at such location. Two probe beams are provided which are coherent with each other having different frequencies or phase. One probe beam is directed towards the location where the disturbance is generated and the other probe beam is directed towards the sample surface at a location away from the disturbance so that it is substantially unaffected by the disturbance but is subject to substantially the same environmental factors as the location where the disturbance is generated. Reflections of the two probe beams are combined and interfere at a detector, The detector output is analyzed to provide the normalized amplitude of the sidebands for determining the physical characteristics or composition of the wafer, including the dose of any ion implants.

52 Claims, 5 Drawing Sheets

OTHER PUBLICATIONS

"Photo–Displacement Imaging," S. Ameri et al., *Electronics Newsletter*, vol. 17, No. 10, May 14, 1982 pp. 337–338.

Product literature on Ion Dose Monitor PA–400 of Kobelco, Kobe Steel Ltd.

"Analysis and Applications of Photothermal Microscopy," J.T. Fanton, G.L. Report No. 4733, Internal Memorandum DE–FG03–87ER13797, Jun. 1990, pp. 1–133.

"Photodisplacement Measurement by Interferometric Laser Probe," H. Takamatsu et al., *Japanese Journal of Applied Physics*, vol. 29, No. 12, Dec. 12, 1990, pp. 2847–2850.

"A New Method of Photothermal Displacement Measurement by Laser Interferometric Probe, Its Mechanism and Applications to Evaluation of Lattice Damage in Semiconductors," S. Sumie et al., *Japanese Journal of Applied Physics*, vol. 31, Part 1, No. 11, Nov. 1992, pp. 3575–3583.

"Effects of ambient gas on photo–acoustic displacement measurement by laser interferometric probe," S. Sumie et al., *Japanese Journal of Applied Physics*, vol. 74, No. 11, Dec. 1, 1993, pp. 6530–6533.

Analysis of lattice defects induced by ion implantation with photo–acoustic displacement measurements, S. Sumie et al., *Japanese Journal of Applied Physics*, vol. 76, No. 10, Nov. 15, 1994, pp. 5681–5689.

"Characteristics of photoacoustic displacement for silicon damaged by ion implantation," H. Takamatsu et al., *Japanese Journal of Applied Physics*, vol. 78, No. 3, Aug. 1, 1995, pp. 1504–1509.

Photothermal Radiometric Microscopy, S.J. Sheard, Thesis submitted for the degree of Doctor of Philosophy of the University of London, Department of Electronic and Electrical Engineering, University Collect London, Oct. 1987, pp. 1–184.

Dual–probe laser interferometer, J. Huang et al., *Journal of the Acoustic Society of America*, 90(3), Sep. 1991, pp. 1269–1274.

International Search Report mailed Feb. 24, 2000.

* cited by examiner

INTERFEROMETRIC SYSTEM FOR MEASUREMENT DISTURBANCE OF A SAMPLE

This application is a continuation of Ser. No. 09/166,614 now filed Oct. 5, 1998 abandoned.

BACKGROUND OF THE INVENTION

This invention relates in general to nondestruction evaluation of sample surfaces, and in particular, to an interferometric system for nondestructive evaluation of samples. There is considerable interest in developing analytical tools for analyzing properties of materials, especially in the semiconductor industry. In particular, nondestructive evaluation of semiconductor and other materials will yield valuable information for the design and manufacture of electronic components.

For example, analytical tools suitable for measuring the dose of ion implants can yield valuable information in the design and manufacture of integrated circuit components.

In U.S. Pat. Nos. 4,521,118 and 5,522,510, Rosencwaig proposes a system for measuring thermal waves and thickness of thin films. A laser beam is directed onto a sample periodically to heat the sample. The heating of the sample causes local surface displacement, where such surface displacement causes a change in the local surface slope. The change in the local surface slope is detected by means of a laser probe beam to nondestructively evaluate the properties of the sample.

U.S. Pat. No. 5,298,970 proposes an interferometer for measuring thermal expansion displacement. A sample is heated cyclically by a laser beam which is modulated in intensity. A measuring beam is split into a first beam directed to a mirror as a reference and a second beam directed to the sample. Reflections of the two beams interfere to give a measurement of the thermal displacement.

Another system that can be used for nondestructive evaluation of sample surfaces is spectroscopic ellipsometry, such as the one described in U.S. Pat. No. 5,608,526. While spectroscopic ellipsometry may be useful for measuring doses of arsenic implants, spectroscopic ellipsometry lacks adequate sensitivity for measuring boron implants.

Most of the above-described systems are not entirely satisfactory for nondestructive evaluation of samples, and especially for measuring low dose boron ion implants. It is therefore desirable to provide an improved system with improved characteristics over the above-described techniques.

SUMMARY OF THE INVENTION

When a portion of the surface of the sample is heated by means of a beam of radiation, the portion changes its physical characteristics. Such characteristics include reflectivity and local displacement of the surface as well as other physical changes. Such changes in the physical characteristics of the portion of the sample surface is referred to as disturbance of the sample. Thus when a pump beam of radiation is applied to a location of a sample, this results in a disturbance of the sample at that location. Two probe beams of radiation coherent with each other are directed towards the sample, with one probe beam directed to the location of the sample where disturbance is created by the pump beam and the second probe beam to a second location of the sample adjacent to the disturbed location but substantially undisturbed by the pump beam. The two probe beams may have different frequencies or be phase shifted relative to one another. The disturbance may be measured by interfering reflections of the two probe beams at a detector. The disturbance so measured may be compared to a reference for determining the dose of ion implants in a semiconductor material.

BRIEF DESCRIPTION OF THE DRAWINGS

For simplicity in description, identical components in this application are identified by the same numerals.

DETAILED DESCRIPTION OF THE PREFERRED EMBODIMENT

Figure 1:
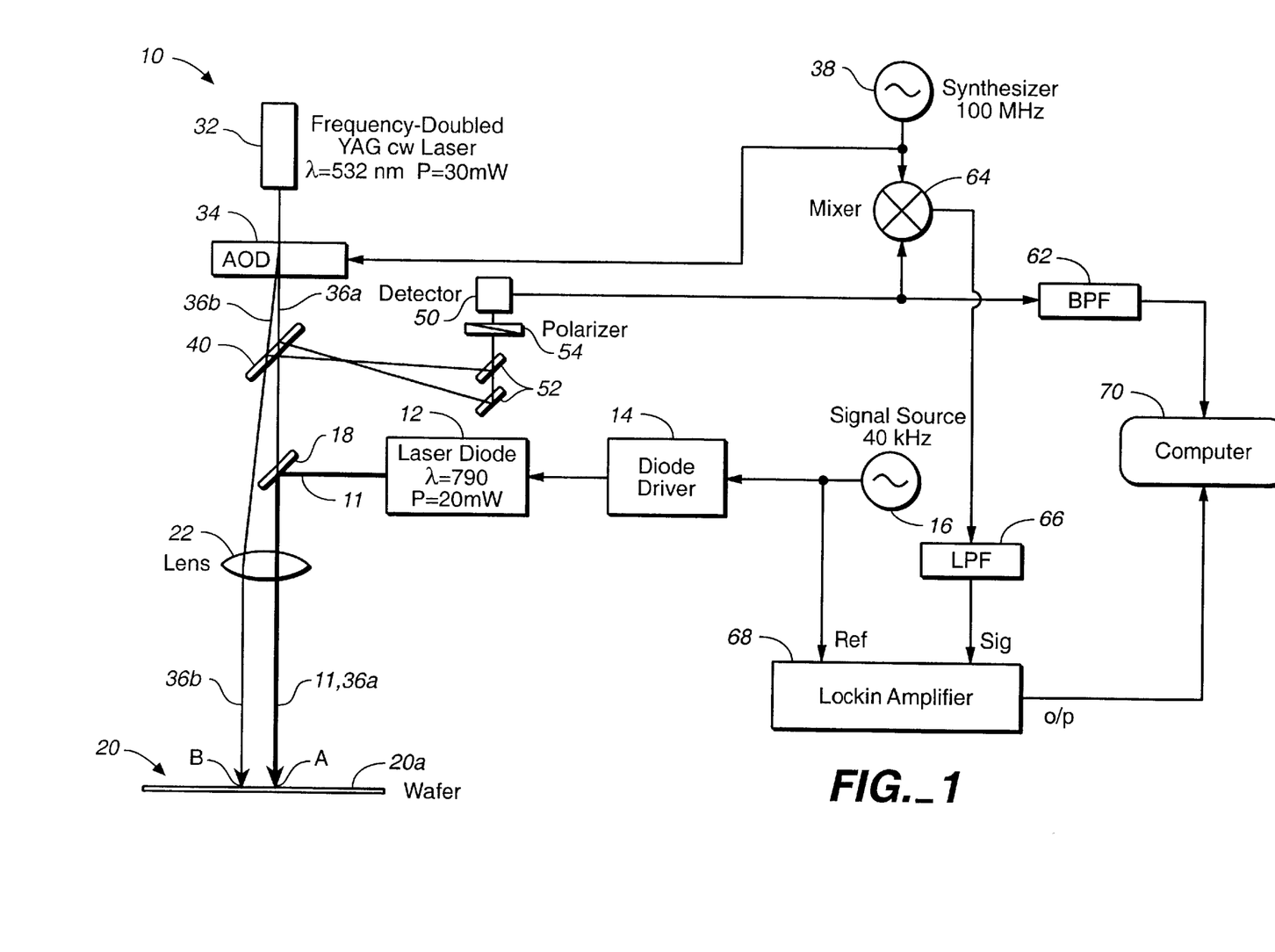
FIG. 1 is a schematic view of an interferometric system for measuring the disturbance and ion dose of a semiconductor wafer to illustrate the preferred embodiment of the invention.

FIG. 1 is a schematic diagram of an interferometric system 10 for measuring the disturbance at a location and determining the ion dose of a semiconductor wafer to illustrate the preferred embodiment of the invention. As shown in FIG. 1, the pump beam 11 of radiation from laser diode 12 is modulated at a frequency such as 40 kHz by means of a diode driver 14 and a signal source 16. The modulated laser pump beam 11 is reflected by a beam splitter 18 towards the surface 20a of a semiconductor wafer 20, at location A of the surface 20a. The pump radiation beam 11 periodically heats surface 20a at location A, causing disturbance of the surface at such location. In order to measure the disturbance, two probe beams are provided, both probe beams originating from a laser 32 which may be a frequency-doubled YAGcw laser supplying radiation at a wavelength of 532 nanometers and a power of 30 milliwats.

In the preferred embodiment, a beam of radiation from laser 32 is passed through an acousto-optic deflector (AOD) 34 which passes a zeroth order beam 36a without deflection or change in frequency and deflects as well as upshifts in frequency a first order beam 36b, thereby generating two probe beams that are coherent with each other but different in frequency. Deflector 34 is controlled by synthesizer 38 at 100 MHz, so that the first order probe beam 36b is upshifted by a carrier frequency of 100 MHz compared to the zeroth order beam 36a. The two probe beams pass through a beam spitter 40 and focused by lens 22 towards surface 20a of the wafer 20. The zeroth order beam 36a also passes through beam splitter 18 on its way to the wafer.

The zeroth order beam 36a is positioned so that it is directed substantially at location A to which the pump beam 11 is also directed. Deflector 34 and lens 22 are so positioned and the driving signal applied to the deflector is such that the first order beam 36b is directed to a location B on surface 20a of the wafer 20 where location B is spaced apart from location A to the extent that the portion of the first surface 20a of the wafer at location B is substantially unaffected by the pump beam 11, but where location B is subject to substantially the same environmental factors that are affecting surface 20a at location A, such as temperature and mechanical vibrations as well as other environmental factors. In the preferred embodiment, locations A and B are spaced apart by one-half to 100 spot sizes, and more preferably by ½ to 10 spot sizes. In other words, if x is the maximum dimension (diameter for circular spots and length of major axis for elliptical spots) of the spots at locations A, B of beams 36a, 36b, then the illuminated spots at A and B are spaced apart by about (½)x to 100x, and more preferably by about 2x to 10x.

Both probe beams are reflected by surface 20a of the wafer, where the reflection of probe beam 36a is modulated by the disturbance caused by the pump beam 11. The reflections of the two probe beams are collected by lens 22 and portions of the two reflections are diverted and reflected by beam splitter 40 towards the detector 50 after reflection by mirrors 52 and passage through polarizer 54.

Figure 4:
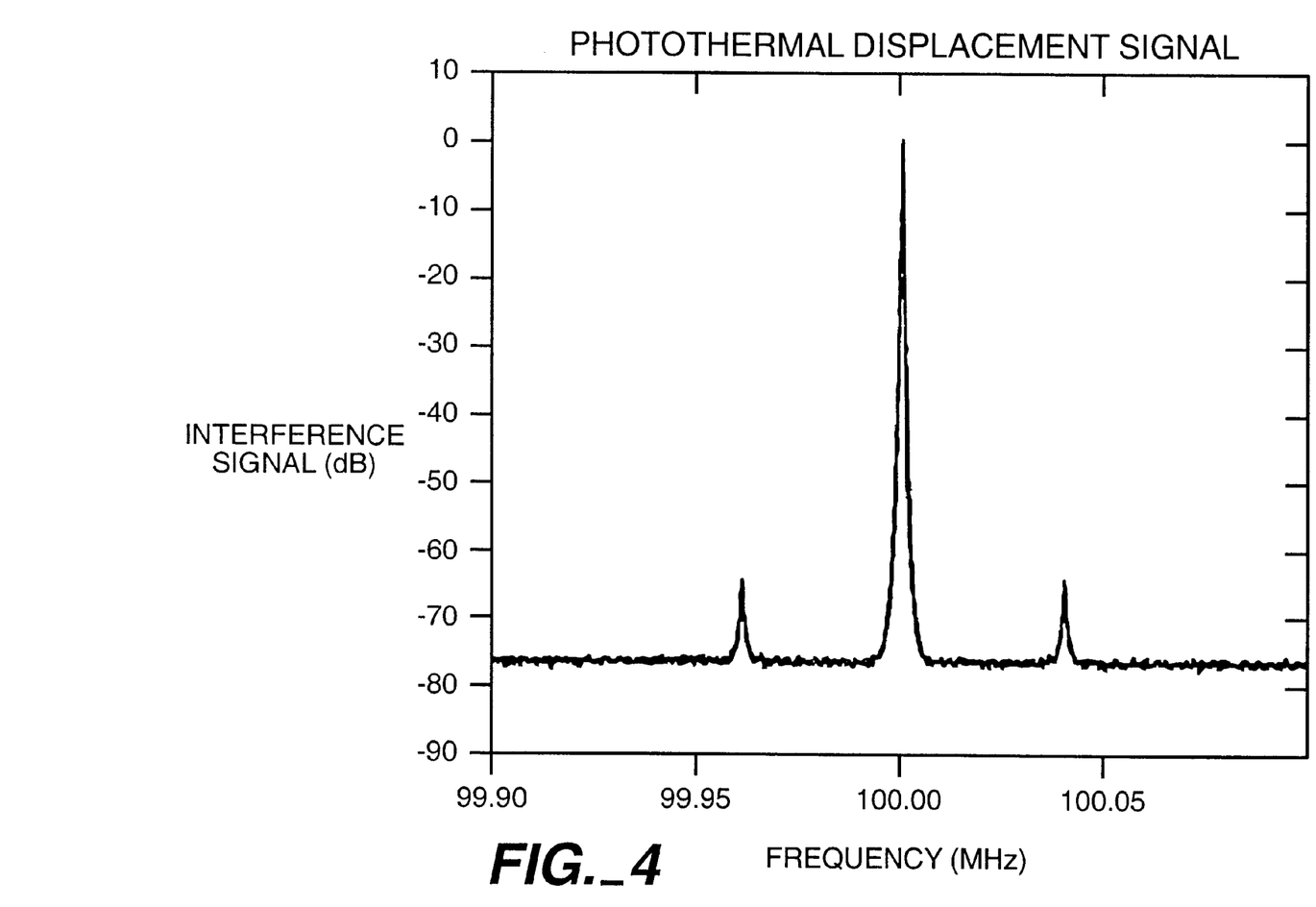
FIG. 4 is a graphical plot of an interference signal against frequency to illustrate the operation of the embodiments of FIGS. 1–3.

Since the two probe beams 36a, 36b are coherent, the diverted portions of the reflections of the two probe beams will interfere at detector 50. The periodic heating of surface 20a at location A by the pump beam causes photothermal displacement of the surface at such location. Such photothermal displacement causes the reflection of the probe beam 36a to be modulated at the modulation frequency of the pump beam, which is also the frequency of the signal source 16, such as 40 kHz. The frequency of the main signal component detected by detector 50 as a result of interference of the reflections of the two portions of the two probe beams collected by beam splitter 40 is at a carrier frequency 100 MHz, the frequency upshift introduced between the two probe beams by AOD 34 and synthesizer 38. The modulation frequency of 40 kHz introduced by source 16 shows up as two sidebands in the detector output. The output of detector 50 is illustrated in FIG. 4: a main signal at a carrier frequency of 100 MHz and two sidebands at 99.96 and 100.04 MHz. A measure of the photothermal displacement signal can be obtained by measuring the amplitude of the two sidebands as shown in FIG. 4. When the pump beam 11 is turned off, the two side bands in FIG. 4 will disappear.

The Applicants recognized that the normalized amplitudes of the sidebands can be an indication of the physical characteristics or composition of the wafer 20, including the dose of ion implants in the wafer. To obtain such amplitude, the output of detector 50 is passed through a band pass filter 62 which passes substantially signals only at or close to the carrier frequency of 100 MHz, so that the output of band pass filter 62 will yield the amplitude of the main carrier signal at 100 MHz. The output of detector 50 is also sent to a mixer 64 which also receives a 100 MHz signal from synthesizer 38 so that the output of the mixer comprises the Sum and difference between the 100 MHz signal from synthesizer 38 and the output of detector 50. The output of mixer 64 is passed through a low pass filter 66 which filters out the high frequency components above about 100 MHz, thereby leaving only the downshifted sideband signals at or around 40 kHz. The output of filter 66 is further amplified by a lock-in amplifier 68 which is tuned by the signal source 16 to amplify only signals at substantially the frequency of the signal source 16. Thus, the output of lock-in amplifier 68 provides the amplitude of the sideband components of the output of detector 50 in FIG. 4. Computer 70 then computes the ratio between the amplitude of the sideband signals at the output of lock-in amplifier 68 and the amplitude of the main carrier signal at 100 MHz at the output of band pass filter 62, to provide the normalized amplitude of the sidebands. Such normalized amplitude of the sidebands may then be-used to determine the dose of any ion implants in wafer 20. Such normalized amplitude of the sidebands is also a measure of the photothermal displacement of surface 20a and an indication of the physical characteristics of wafer 20.

From FIG. 1, it should also be noted that the two portions of the reflected probe beams diverted by beam splitter 40 and reflected by mirrors 52 towards detector 50 arrive at the detector substantially co-linearly so that an effective interference can be realized. It is noted above that locations A, B are preferably situated so that location B is subject to substantially the same environmental factors that are affecting surface 20a at location A, such as temperature and mechanical vibrations as well as other environmental factors. Since the two beams 36a, 36b are incident at locations A and B, the reflections of the two beams will both be affected in the same manner by such factors, so that interference between the reflections will reduce the effects of such factors on the interferometric measurement and enhances the signal-to-noise ratio of the system.

Figure 5:
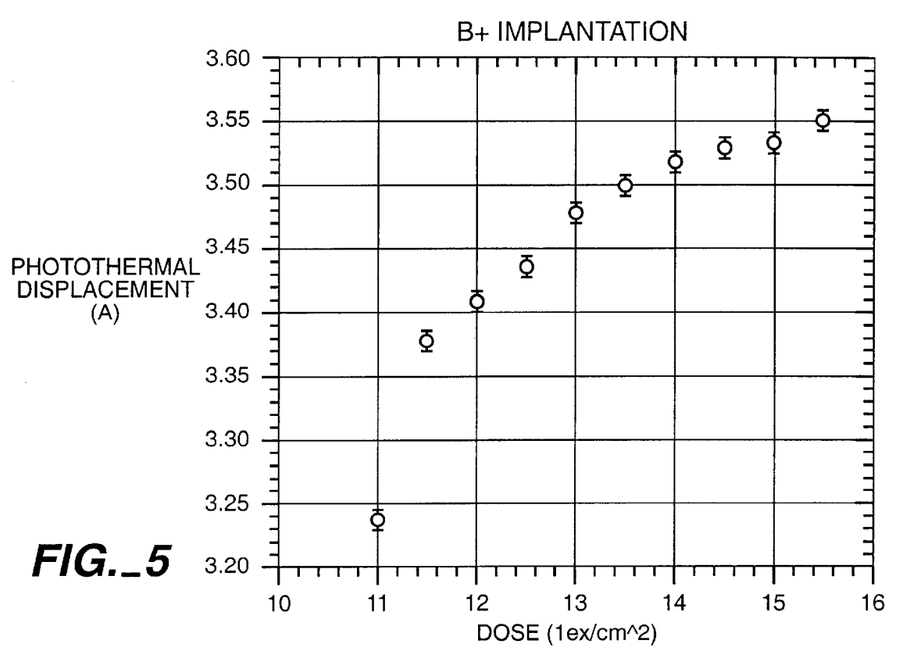
FIG. 5 is a graphical plot of the photothermal displacement as a function of boron ion dose to illustrate a method for determining the boron dose in a semiconducting material after the photothermal displacement of the material has been measured.
Figure 6:
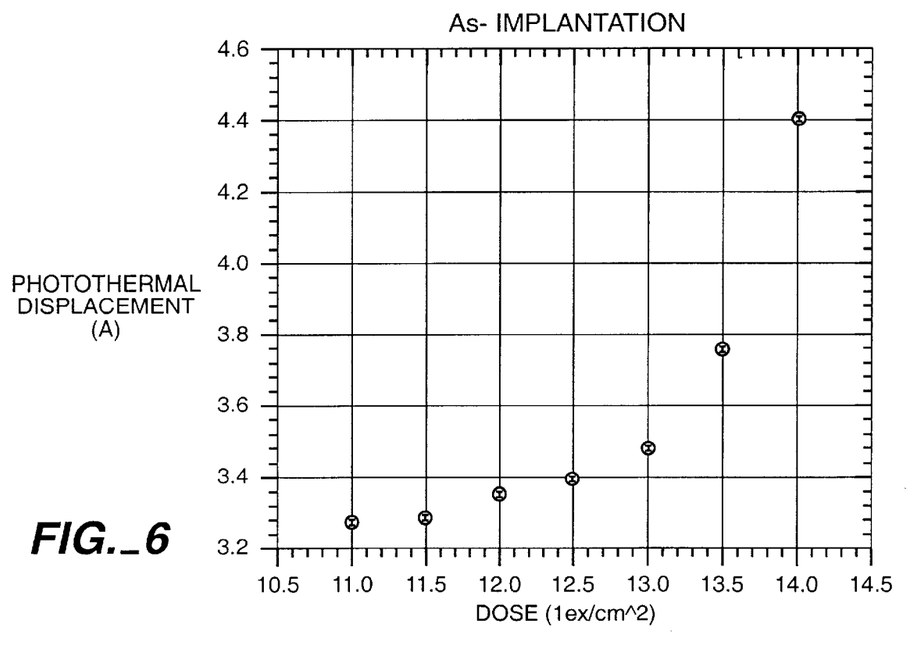
FIG. 6 is a graphical plot of the photothermal displacement as a function of implant dose to illustrate a method for determining the arsenic dose in a semiconductor material after the photothermal displacement of the material has been measured.

FIG. 5 is a graphical plot of measured data obtained for boron doped silicon with the dose ranging from $IE11\ cm^{-2}$ to $IE16\ cm^{-2}$. From FIG. 5, it is seen that the photothermal displacement signal increases steadily with dose of the boron ions. FIG. 6 shows data obtained from arsenic implanted silicon over the same range of dose. A kink is observed at about IE13.5 in FIG. 6, which is in good agreement with measurements using other measurement schemes. Once the normalized photodisplacement has been obtained as described above in reference to FIG. 1, the graphical plots of FIGS. 5 and 6 may be used, for example, to determine from the measurements the dose of the boron or arsenic implant at location A in wafer 20.

Figure 2:
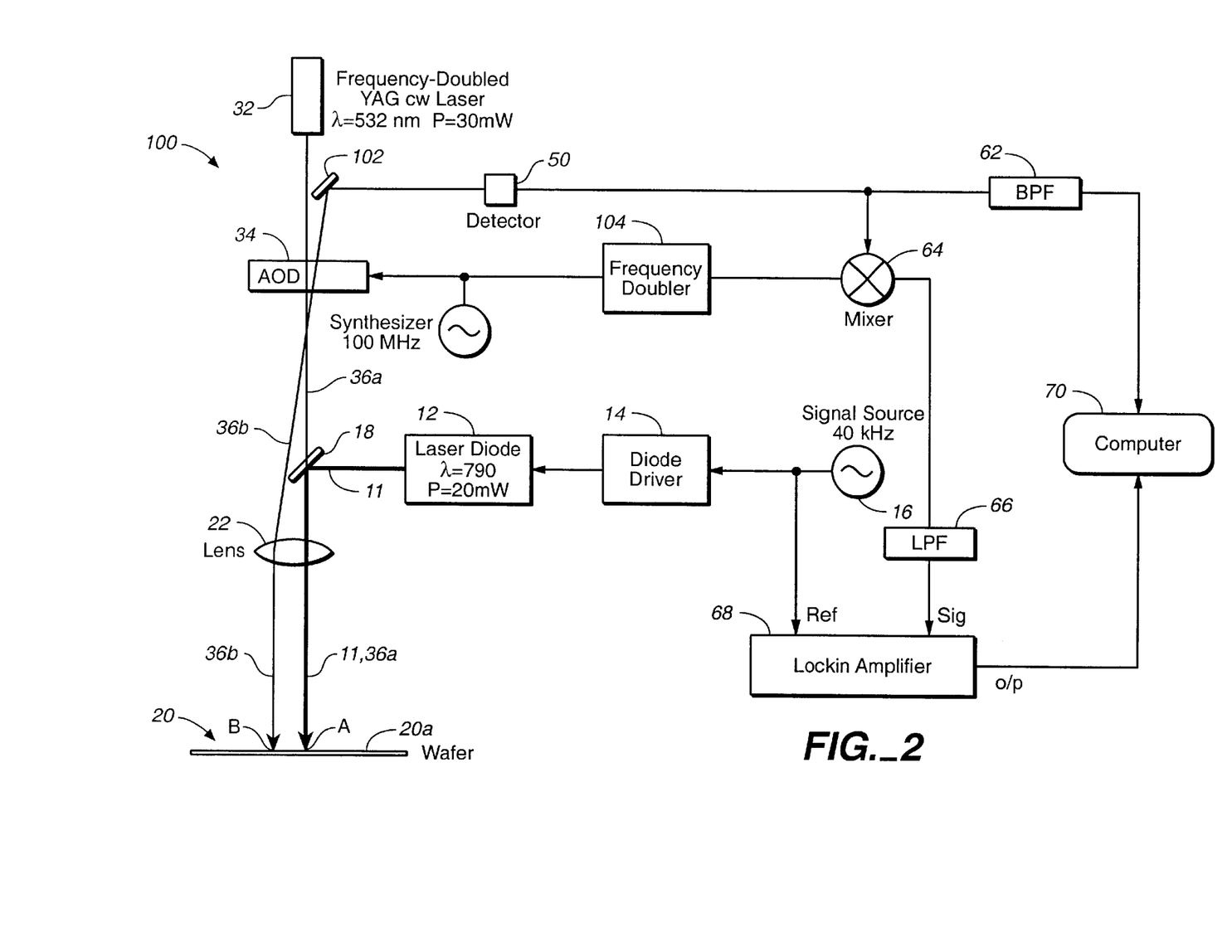
FIG. 2 is a schematic view of an interferometric system for measuring the disturbance and determining the ion dose of a semiconductor wafer to illustrate an alternative embodiment of the invention.

FIG. 2 is a schematic view of an interferometric system for measuring disturbance of a sample to illustrate an alternative embodiment of the invention. In reference to FIGS. 1 and 2, instead of using a beam splitter 40 to divert portions of the reflections of the two probe beams from surface 20a as in FIG. 1, system 100 of FIG. 2 uses the AOD 34 to recombine the reflections of the two probe beams from surface 20a of the wafer and the recombined beam is reflected by means of a mirror 102 towards the detector 50. The reflection of the zeroth order beam 36a will be downshifted in frequency by about 100 MHz and diverted by the-AOD 34. towards mirror 102 after passing through the AOD. However, at least a part of the reflection of the first order beam 36b will be unaffected in frequency and not deflected when it passes through the AOD 34 on its way to mirror 102 and the detector 50, so that the carrier frequency present in the output of detector 50 will be twice the frequency of the synthesizer 38, or in other words, at about 200 MHz. For this reason, in order for the mixer 64 to perform the mixing function in order to downshift frequency of the output of detector 50 from the MHz range to the kHz range, a frequency doubler 104 is employed. Aside from such variation, the alternative embodiment of FIG. 2 is substantially the same as the embodiment of FIG. 1. As shown in FIG. 2, the reflections of the two probe beams are co-linearized by means of the AOD 34.

Figure 3:
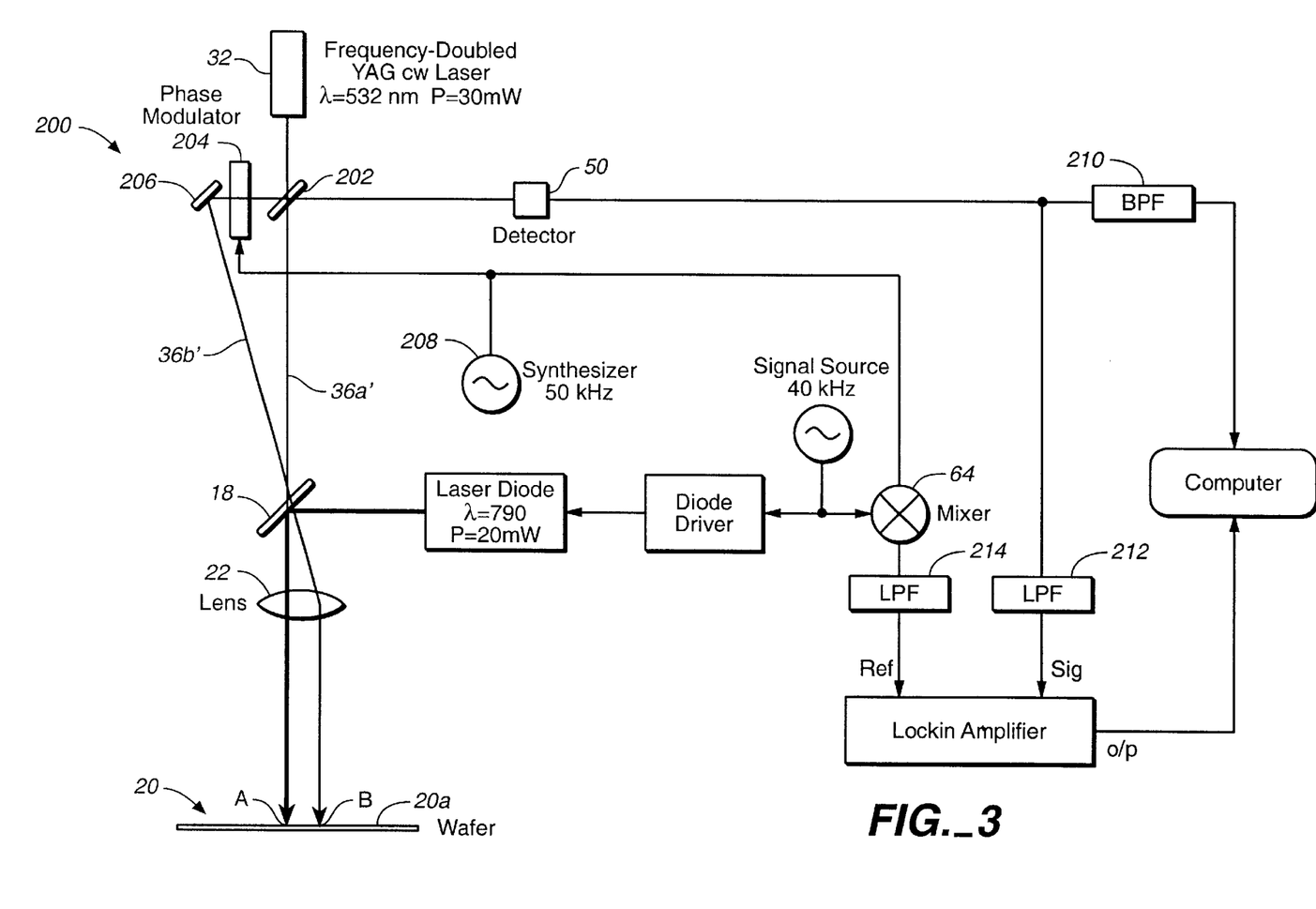
FIG. 3 is a schematic view of an interferometric system for measuring the disturbance and determining the ion dose of a semiconductor wafer to illustrate yet another alternative embodiment of the invention.

FIG. 3 is a schematic view of an interferometric system for measuring disturbance of a sample to illustrate yet another embodiment of the invention. System 200 of FIG. 3 differs from that of FIGS. 1 and 2 in the manner in which the two probe beams are generated. Instead of using an AOD as in the embodiments of FIGS. 1 and 2, the radiation beam from laser 32 is split into two beams with the same frequency by means of a beam splitter 202. The beam that passes through the beam splitter 202 is now one of the probe beams 36a' which propagates through beam splitter 18 and lens 22 to location A on surface 20a. The radiation from laser 32 that is reflected by beam splitter 202 is phase shifted by phase modulator 204 without affecting the frequency of such radiation to become the second probe beam 36b'. Beam 36b' is reflected by mirror 206 towards beam splitter 18 and lens 22 which bends and focuses the beam to location B so that it is substantially parallel to beam 36a'. The reflection of probe beam 36b' is also focused and bent by lens 22 along its original incoming path towards mirror 206, phase modulator 204 and passes beam splitter 202 to detector 50. The reflection of probe beam 36a' passes through lens 22 and is reflected by beam splitter 202 also towards detector 50, so that the reflections of the two probe beams arrive co-linearly at detector 50. The phase modulator 204 again shifts the phase of the reflection of probe beam 36b' so that, upon reaching the detector 50, the phase shift of such reflection relative to beam 36a' is twice that of the phase shift of beam 36b' relative to beam 36a'.

As known to those skilled in the art, the phase shift between the reflections of two coherent probe beams at detector 50 causes two beat signals in addition to the main signal at the carrier frequency, The phase modulator 204 is controlled by synthesizer 208 at 50 kHz, so that the main signal component in the output of detector 50 is at a carrier frequency of 50 kHz. The 40 kHz modulation of the pump beam causes the reflection of the probe beam 36a' to be modulated at the same frequency, so that the two beat signals appear as two side bands of 10 kHz and 90 kHz. Band pass filter 210 is designed to pass the main signal component at 50 kHz to yield the amplitude of the carrier signal and low pass filter 212 passes only the beat signal at side band frequency of 10 kHz. Mixer 64 receives as inputs the 40 kHz and 50 k(Hz signals from source 16 and synthesizer 208 and provides the sum and difference of these two input frequencies. The 90 kHz signal is filtered out by low pass filter 214, so that only the 10 kHz signals is applied to lock-in amplifier 68. Amplifier 68 amplifies the output of filter 212 substantially only at the 10 kHz frequency to provide the amplitude of the 10 kHz sideband beat signal to computer 70 which then computes the normalized sideband signal in the same manner as that described above in reference to FIG. 1. This normalized sideband signal amplitude may then be used in conjunction with FIGS. 5 and 6 in the manner described above to obtain the dose of the implants at location A in wafer 20 in FIG. 3.

The radiation in the pump and probe beams may include wavelengths in the visible, infrared ultraviolet X-ray rang(e and other wavelengths. The Easers for supplying the pump and probe beams may also be operated at power levels that are different from the values in the above embodiments. The frequencies at which the pump and probe beams are modulated or upshifted/downshifted may also be different from the values in the embodiments above, as long as the modulation frequency of the pump beam is smaller than the frequency upshift/downshift of the probe beam; such and other variations are within the scope of the invention.

While the invention has been described above by reference to various embodiments, it will be understood that changes and modifications may be made without departing from the scope of the invention, which is to be defined only by the appended claims and their equivalents.

What is claimed is:

1. An apparatus for measuring disturbance of a sample, comprising:
   a first source supplying a pump beam of radiation modulated at a modulation frequency to a first location of the sample to cause disturbance at the modulation frequency of the sample at the first location;
   a second source supplying a first probe beam of radiation to substantially the first location of the sample when the sample is disturbed by the pump beam, and a second probe beam to a second location of the sample adjacent to the first location but substantially unaffected by the disturbance, said two probe beams being substantially coherent with each other; wherein the probe beams have frequencies that are different by a carrier frequency;
   a detector;
   optics directing reflections of the two probe beams from the sample towards the detector so that said reflections interfere at the detector; and
   a device analyzing an output of the detector or a signal derived therefrom using the modulation frequency to determine said disturbance of the sample caused by the pump beam.

2. The apparatus of claim 1, further comprising a modulator upshifting frequency of one of the two probe beams so that the probe beams have frequencies that are different by the carrier frequency.

3. The apparatus of claim 2, said modulator being an acousto-optic deflector.

4. The apparatus of claim 1, said device analyzing the detector output or a signal derived therefrom by deriving a ratio of amplitude of sidebands to amplitude at the carrier frequency to determine said disturbance of the sample caused by the pump beam.

5. The apparatus of claim 4, said first source further comprising a modulator modulating a beam so that the modulated beam is the pump beam before the pump beam is supplied to the first location of the sample.

6. The apparatus of claim 5, said modulator modulating the beam at a modulation frequency, so that the disturbance is indicated by signals at the carrier frequency and at modulation frequency, said device including a band pass filter to pass a signal from the detector at the carrier frequency, a mixer to shift a signal from the detector by the frequency of the carrier frequency, and a low pass filter to pass the shifted signal from the mixer at the modulation frequency.

7. The apparatus of claim 6, said device including means for computing said ratio from the amplitude of the signal at the carrier frequency and that of the shifted signal at the modulation frequency.

8. The apparatus of claim 6, said device further comprising means for amplifying the shifted signal substantially only at the modulation frequency.

9. The apparatus of claim 1, said second source comprising means for splitting a beam of coherent radiation into a zeroth order beam to be the first probe beam and a first order beam to be the second probe beam.

10. The apparatus of claim 9, said splitting means including an acousto-optic deflector.

11. The apparatus of claim 1, said first probe beam and the pump beam traveling along substantially the same optical path.

12. The apparatus of claim 1, said first and second beam spatially separated by about 2 to 10 spot sizes.

13. The apparatus of claim 1, said disturbance being a photodisplacement of the surface of the sample or change in reflectivity of the sample.

14. The apparatus of claim 1, said optics including an acousto-optic deflector which combines the reflections of the two probe beams so that the optics directs said combination to the detector.

15. The apparatus of claim 1, said optics comprising a splitter that diverts a portion of each of the reflections of the two probe beams so that the optics directs said diverted portions to the detector.

16. A method for measuring disturbance of a sample, comprising:

supplying a pump beam of radiation modulated at a modulation frequency to a first location of the sample to cause disturbance at the modulation frequency of the sample at the first location;

supplying a first probe beam of radiation to substantially the first location of the sample when the sample is disturbed by the pump beam, and a second probe beam to a second location of the sample adjacent to the first location but substantially unaffected by the disturbance, said two probe beams being substantially coherent with each other; wherein the probe beams have frequencies that are different by a carrier frequency;

directing reflections of the two probe beams from the sample towards a detector so that said reflections interfere at the detector; and analyzing an output of the detector or a signal derived therefrom using the modulation frequency to determine said disturbance of the sample caused by the pump beam.

17. The method of claim 16, further comprising upshifting frequency of one of the two probe beams so that the probe beams have frequencies that are different by the carrier frequency.

18. The method of claim 16, wherein said analyzing analyzes the detector output or a signal derived therefrom by deriving a ratio of amplitude of sidebands to amplitude at the carrier frequency to determine said disturbance of the sample caused by the pump beam.

19. The method of claim 18, further comprising modulating a beam to become the pump beam before the pump beam is supplied to the first location of the sample.

20. The method of claim 19, wherein said modulating modulates the beam at a modulation frequency, so that the disturbance is indicated by signals at the carrier frequency and at sideband frequencies given by the sum and difference between the carrier frequency and the modulation frequency, and wherein said analyzing includes filtering a signal from the detector to obtain its component at the carrier frequency, shifting a signal from the detector by the frequency of the carrier frequency, and filtering the shifted signal to obtain its component at the modulation frequency.

21. The method of claim 20, wherein said analyzing includes computing said ratio from the amplitude of the signal at the carrier frequency and that of the shifted signal at the modulation frequency.

22. The method of claim 20, wherein said analyzing further comprises amplifying the shifted signal substantially only at the modulation frequency.

23. The method of claim 16, wherein said probe beams supplying comprises splitting a beam of coherent radiation into a zeroth order beam to be the first probe beam and a first order beam to be the second probe beam.

24. The method of claim 16, said first probe beam and the pump beam traveling along substantially the same optical path.

25. The method of claim 16, said first and second beam spatially separated by about 2 to 10 spot sizes.

26. The method of claim 16, said disturbance being a photodisplacement of the surface of the sample or change in reflectivity of the sample.

27. An apparatus for measuring dose of an ion implant of a sample, comprising:

a first source supplying a pump beam of radiation modulated at a modulation frequency to a first location of the sample to cause disturbance at the modulation frequency of the sample at the first location;

a second source supplying a first probe beam of radiation to substantially the first location of the sample when the sample is disturbed by the pump beam, and a second probe beam to a second location of the sample adjacent to the first location but substantially unaffected by the disturbance, said two probe beams being substantially coherent with each other; wherein the probe beams have frequencies that are different by a carrier frequency;

a detector;

optics directing reflections of the two probe beams from the sample towards the detector so that said reflections interfere at the detector;

a device analyzing an output of the detector or a signal derived therefrom using the modulation frequency to determine said disturbance of the sample caused by the pump beam; and a computer comparing said disturbance of the sample caused by the pump beam to a reference to determine dose of an ion implant of a sample.

28. The apparatus of claim 27, further comprising a modulator upshifting frequency of one of the two probe beams so that the probe beams have frequencies that are different by the carrier frequency.

29. The apparatus of claim 28, said modulator being an acousto-optic deflector.

30. The apparatus of claim 27, said device analyzing the detector output or a signal derived therefrom by deriving a ratio of amplitude of sidebands to amplitude at the carrier frequency to determine said disturbance of the sample caused by the pump beam.

31. The apparatus of claim 30, further comprising a modulator modulating the pump beam before the pump beam is supplied to the first location of the sample.

32. The apparatus of claim 31, said modulator modulating the pump beam at a modulation frequency, so that the disturbance is indicated by signals at the carrier frequency and at sideband frequencies given by the sum and difference between the carrier frequency and the modulation frequency, said device including a band pass filter to pass a signal from the detector at the carrier frequency, a mixer to shift a signal from the detector by the frequency of the carrier frequency, and a low pass filter to pass the shifted signal from the mixer at the modulation frequency.

33. The apparatus of claim 32, said device including means for computing said ratio from the amplitude of the signal at the carrier frequency and that of the shifted signal at the modulation frequency.

34. The apparatus of claim 32, said device further comprising means for amplifying the shifted signal substantially only at the modulation frequency.

35. The apparatus of claim 27, said second source comprising means for splitting a beam of coherent radiation into a zeroth order beam to be the first probe beam and a first order beam to be the second probe beam.

36. The apparatus of claim 35, said splitting means including an acousto-optic deflector.

37. The apparatus of claim 27, said first probe beam and the pump beam traveling along substantially the same optical path.

38. The apparatus of claim 27, said first and second beam spatially separated by about 2 to 10 spot sizes.

39. The apparatus of claim 27, said disturbance being a photodisplacement of the surface of the sample or change in reflectivity of the sample.

40. The apparatus of claim 27, said optics including an acousto-optic deflector which combines the reflections of the two probe beams so that the optics directs said combination to the detector.

41. The apparatus of claim 27, said optics comprising a splitter that diverts a portion of each of the reflections of the two probe beams so that the optics directs said diverted portions to the detector.

42. A method for measuring for measuring dose of an ion implant of a sample, comprising:

supplying a pump beam of radiation modulated at a modulation frequency to a first location of the sample to cause disturbance at the modulation frequency of the sample at the first location;

supplying a first probe beam of radiation to substantially the first location of the sample when the sample is disturbed by the pump beam, and a second probe beam to a second location of the sample adjacent to the first location but substantially unaffected by the disturbance, said two probe beams being substantially coherent with each other, wherein the probe beams have frequencies that are different by a carrier frequency;

directing reflections of the two probe beams from the sample towards a detector so that said reflections interfere at the detector;

analyzing an output of the detector or a signal derived therefrom using the modulation frequency to determine said disturbance of the sample caused by the pump beam; and comparing said disturbance of the sample caused by the pump beam to a reference to determine dose of an ion implant of a sample.

43. The method of claim 42, further comprising upshifting frequency of one of the two probe beams so that the probe beams have frequencies that are different by the carrier frequency.

44. The method of claim 42, wherein said analyzing analyzes the detector output or a signal derived therefrom by deriving a ratio of amplitude of sidebands to amplitude at the carrier frequency to determine said disturbance of the sample caused by the pump beam.

45. The method of claim 44, further comprising modulating a beam to become the pump beam before the pump beam is supplied to the first location of the sample.

46. The method of claim 45, wherein said modulating modulates the beam at a modulation frequency, so that the disturbance is indicated by signals at the carrier frequency and at sideband frequencies given by the sum and difference between the carrier frequency and the modulation frequency, and wherein said analyzing includes filtering a signal from the detector to obtain its component at the carrier frequency, shifting a signal from the detector by the frequency of the carrier frequency, and filtering the shifted signal to obtain its component at the modulation frequency.

47. The method of claim 46, wherein said analyzing includes computing said ratio from the amplitude of the signal at the carrier frequency and that of the shifted signal at the modulation frequency.

48. The method of claim 46, wherein said analyzing further comprises amplifying the shifted signal substantially only at the modulation frequency.

49. The method of claim 42, wherein said probe beams supplying comprises splitting a beam of coherent radiation into a zeroth order beam to be the first probe beam and a first order beam to be the second probe beam.

50. The method of claim 42, said first probe beam and the pump beam traveling along substantially the same optical path.

51. The method of claim 42, said first and second beam spatially separated by about 2 to 10 spot sizes.

52. The method, of claim 51, said disturbance being a photodisplacement of the surface of the sample or change in reflectivity of the sample.

* * * * *